United States Patent [19]
Narciso, Jr.

[11] Patent Number: 6,110,188
[45] Date of Patent: Aug. 29, 2000

[54] ANASTOMOSIS METHOD

[75] Inventor: Hugh L. Narciso, Jr., Mountain View, Calif.

[73] Assignee: Corvascular, Inc., Palo Alto, Calif.

[21] Appl. No.: 09/037,216

[22] Filed: Mar. 9, 1998

[51] Int. Cl.[7] .................................................. A61B 17/00
[52] U.S. Cl. ............................................................ 606/153
[58] Field of Search .................................. 606/151–154, 606/191–195; 128/898; 623/1, 12, 13, 11; 604/96, 53

[56] References Cited

U.S. PATENT DOCUMENTS

| | | |
|---|---|---|
| 3,254,650 | 6/1966 | Collito . |
| 3,254,651 | 6/1966 | Collito . |
| 3,519,187 | 7/1970 | Kapitanov et al. . |
| 3,561,448 | 2/1971 | Peternel . |
| 3,657,744 | 4/1972 | Ersek . |
| 3,683,926 | 8/1972 | Suzuki . |
| 3,774,615 | 11/1973 | Lim et al. . |
| 3,805,793 | 4/1974 | Wright . |
| 4,350,160 | 9/1982 | Kolesov et al. . |
| 4,352,358 | 10/1982 | Angelchik . |
| 4,366,819 | 1/1983 | Kaster . |
| 4,368,736 | 1/1983 | Kaster . |
| 4,523,592 | 6/1985 | Daniel . |
| 4,553,542 | 11/1985 | Schenck et al. . |
| 4,593,693 | 6/1986 | Schenck . |
| 4,607,637 | 8/1986 | Berggren et al. . |
| 4,624,255 | 11/1986 | Schenck et al. . |
| 4,624,257 | 11/1986 | Berggren et al. . |
| 4,657,019 | 4/1987 | Walsh et al. . |
| 4,665,906 | 5/1987 | Jervis . |
| 4,712,551 | 12/1987 | Rayhanabad . |
| 4,733,665 | 3/1988 | Palmaz . |
| 4,747,407 | 5/1988 | Liu et al. . |
| 4,776,337 | 10/1988 | Palmaz . |
| 4,787,386 | 11/1988 | Walsh et al. . |
| 4,873,975 | 10/1989 | Walsh et al. . |

(List continued on next page.)

FOREIGN PATENT DOCUMENTS

| | | |
|---|---|---|
| 0791332 A1 | 8/1997 | European Pat. Off. . |
| 24 50 877 | 5/1975 | Germany . |
| WO 96/25897 | 8/1996 | WIPO . |
| PCT/US97/02044 | 8/1997 | WIPO . |
| WO 98/19608 | 5/1998 | WIPO . |
| WO 98/19618 | 5/1998 | WIPO . |
| WO 98/19629 | 5/1998 | WIPO . |
| WO 98/19630 | 5/1998 | WIPO . |
| WO 98/19631 | 5/1998 | WIPO . |
| WO 98/19632 | 5/1998 | WIPO . |
| WO 98/19634 | 5/1998 | WIPO . |
| WO 98/19636 | 5/1998 | WIPO . |
| WO 98/55027 | 12/1998 | WIPO . |

OTHER PUBLICATIONS

Carter et al., "Direct Nonsuture Coronary Artery Anastomosis in the Dog" *Ann. Surg.*(1958)148:212–218.

Coggia et al., "Anastomosis over a stent for heavily calcified arteries" *Ann. Vasc. Surg.* (1995)9[suppl]:S39–S44.

(List continued on next page.)

*Primary Examiner*—Michael Buiz
*Assistant Examiner*—Vikki Trinh
*Attorney, Agent, or Firm*—Morrison & Foerster LLP

[57] ABSTRACT

A method for sealingly joining a graft vessel to a target vessel at an anastomosis site, the target vessel having an opening formed therein. The method includes positioning a fastener made from a deformable material radially adjacent to a free end portion of the graft vessel. The material is transformable between a non-fluent state and a fluent state, upon application of energy to the material. The method further includes inserting at least the free end portion of the graft vessel in the target vessel through the opening in the target vessel. Energy is then supplied to the deformable material at an intensity sufficient to transform the material into the fluent state. The free end portion of the graft is radially expanded to expand the graft vessel into intimate contact with an inner wall of the target vessel. The energy supply is discontinued so that the material returns to its non-fluent state to sealingly secure the graft vessel to the target vessel.

46 Claims, 9 Drawing Sheets

U.S. PATENT DOCUMENTS

| | | |
|---|---|---|
| 4,907,591 | 3/1990 | Vasconcellos et al. . |
| 4,917,087 | 4/1990 | Walsh et al. . |
| 4,917,090 | 4/1990 | Berggren et al. . |
| 4,917,091 | 4/1990 | Berggren et al. . |
| 4,917,114 | 4/1990 | Green et al. . |
| 5,100,429 | 3/1992 | Sinofsky et al. . |
| 5,119,983 | 6/1992 | Green et al. . |
| 5,197,978 | 3/1993 | Hess . |
| 5,213,580 | 5/1993 | Slepian et al. . |
| 5,328,471 | 7/1994 | Slepian . |
| 5,336,233 | 8/1994 | Chen . |
| 5,366,462 | 11/1994 | Kaster et al. . |
| 5,443,947 | 8/1995 | Lok . |
| 5,456,712 | 10/1995 | Maginot . |
| 5,478,354 | 12/1995 | Tovey et al. . |
| 5,503,635 | 4/1996 | Sauer et al. . |
| 5,522,834 | 6/1996 | Fonger et al. . |
| 5,522,881 | 6/1996 | Lentz . |
| 5,562,690 | 10/1996 | Green et al. . |
| 5,575,815 | 11/1996 | Slepian et al. . |
| 5,662,609 | 9/1997 | Slepian . |
| 5,662,712 | 9/1997 | Pathak et al. . |
| 5,665,063 | 9/1997 | Roth et al. . |
| 5,674,287 | 10/1997 | Slepian et al. . |
| 5,683,453 | 11/1997 | Palmaz ........................................ 623/1 |
| 5,695,504 | 12/1997 | Gifford, III et al. . |
| 5,698,189 | 12/1997 | Rowe et al. . |
| 5,899,935 | 5/1999 | Ding . |
| 5,902,332 | 5/1999 | Schatz . |

OTHER PUBLICATIONS

Costello et al., "Sutureless end–to–end bowel anastomosis using Nd:YAG and water–soluble intraluminal stent" *Lasers Surg. Med.* (1990) 10(2):179–184..

Detweiler et al., "Sliding, absorbable, reinforced ring and an axially driven stent placement device for sutureless fibrin glue gastrointestinal anastomosis" *J. Invest. Surg.* (1996)9(6):495–504.

Detweiler et al., "Sutureless anastomosis of the small intestine and the colon in pigs using an absorbable intraluminal stent and fibrin glue" *J. Invest. Surg.* (1995) 8(2):129–140.

Goetz et al., "Internal Mammary–Coronary Artery Anastomosis: A Nonsuture Method Employing Tantalum Rings" *J. Thorac. Cardio Surg.* (1961)41:378–386.

Hardy, "Non–suture anastomosis: The historical development" *N.Z.J. Surg.* (1990) 60:625–633.

Jiao et al., "Anastomosis of small artery using ZT medical adhesive and soluble stent" *Chung Hua Cheng Hsing Shao Shang Wai Ko Tsa Chih*(1994) 10(5):334–336.

Kamiji et al., "Microvascular anastomosis using polyethylene glycol 4000 and fibrin glue" *British J. Plastic Surg.* (1989) 42:54–58.

Mikaelsson et al., "Nonsuture end–to–end microvascular anastomosis using intravascular stents" *Ann. Chir. Gynaecol.* (1996) 85(1):36–39.

Moskovitz et al., "Microvascular anastomoses utilizing new intravascular stents" *Ann. Plast. Surg.* (1994) 32:612–618.

Rivetti et al., "Initial experience using an intraluminal shunt during revascularization of the beating heart" *Ann. horac. Surg.* (1997) 63:1742–1747.

Robinson et al., "Transient ventricular asystole using adenosine during minimally invasive and open sternotomy coronary artery bypass grafting" *Ann. Thorac. Surg.*(1997)63:S30–S34.

Rösch et al., "Experimental intrahepatic portacaval anastomosis: Use of expandable Gianturco stents" *Radiology* (1987) 162(2):481–485.

Schöb et al. "New anastomosis technique for (laparoscopic) instrumental small–diameter anastomosis" *Surg. Endosc.* (1995) 9(4):444–449.

Vorwerk et al., "Sutureless vascular end–to–side anastomosis: An in vivo test of a percutaneous concept in the animal model" *Rofo Fortschr Geb Rontgenstr Neuen Bildgeb Verfahr* (1997) 167(1):83–86.

Wei et al., "The temporary stent technique: an easier method of micro–venous anastomosis" *Br. J. Plast. Surg.*(1982) 35(1):92–95.

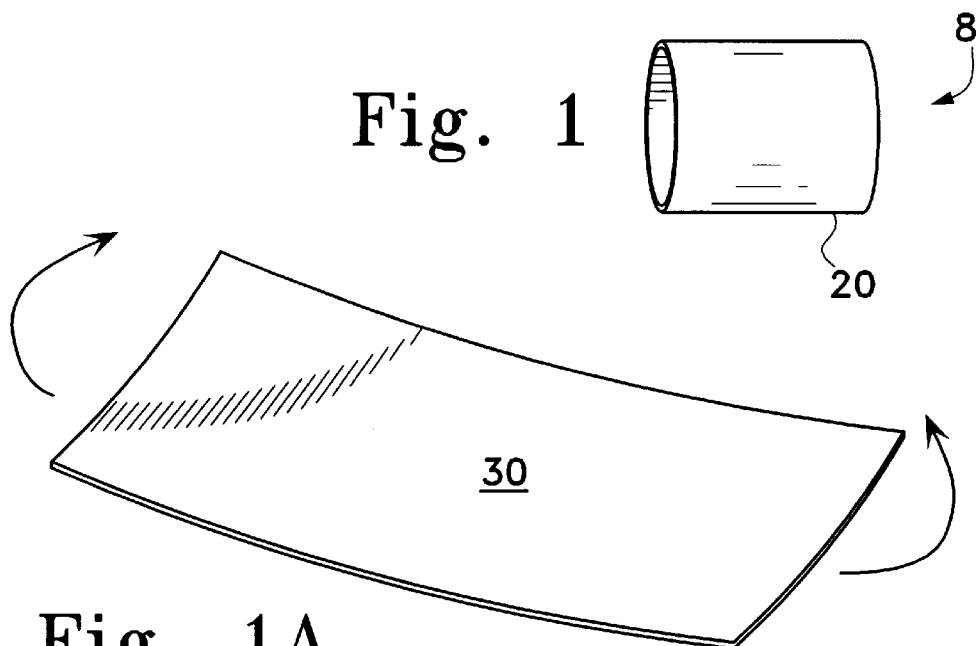
Fig. 1
Fig. 1A
Fig. 1B
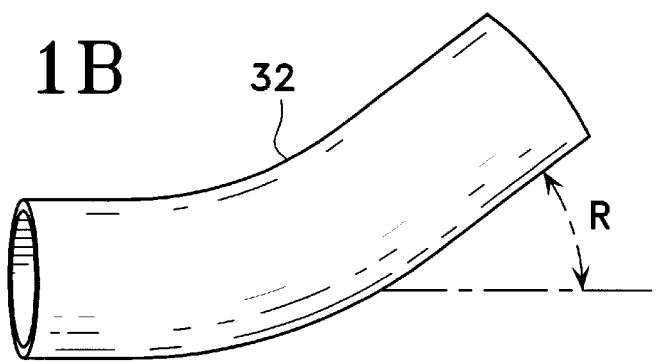
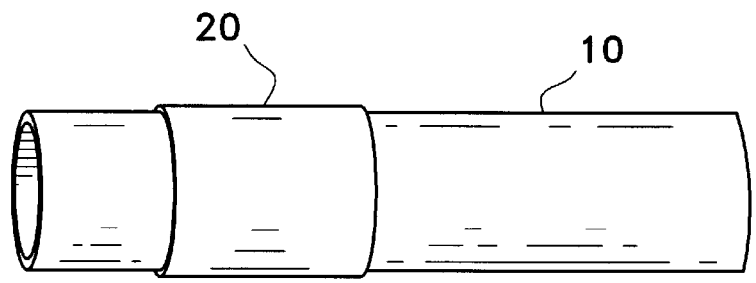
Fig. 2
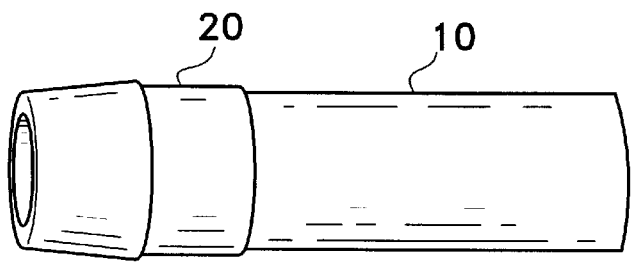
Fig. 3

ANASTOMOSIS METHOD

FIELD OF THE INVENTION

The present invention relates generally to devices and methods for performing a vascular anastomosis and, more particularly, to a device for coupling the end of a vessel, such as a coronary bypass graft, to the side wall of a vessel such as a coronary artery.

BACKGROUND OF THE INVENTION

A manifestation of coronary artery disease is the build-up of plaque within the inner walls of the coronary arteries, which causes narrowing or complete closure of these arteries, resulting in insufficient blood flow. This deprives the heart muscle of oxygen and nutrients, leading to ischemia, possible myocardial infarction and even death. When angioplasty is excluded from potential treatments, surgery to alleviate this problem is employed and often involves creating an anastomosis between a coronary artery and a graft vessel to restore a blood flow path to essential tissues. An anastomosis is a surgical procedure by which two vascular structures, such as a graft vessel and a coronary artery, are interconnected.

Current methods available for creating an anastomosis include hand suturing the vessels together. Connection of interrupted vessels with stitches has inherent drawbacks. For example, it is difficult to perform and requires great skill and experience on the part of the surgeon due in large part to the extremely small scale of the vessels. For example, the coronary arteries typically have a diameter in the range of between about 1 to 5 mm, and the graft vessels have a diameter on the order of about 1 to 4 mm for an arterial graft such as a thoracic artery, or about 4 to 8 mm for a vein graft such as a saphenous vein. Other drawbacks of connection with stitches are the long duration of the operation, during which period in conventional open-heart coronary artery bypass graft (CABG) surgery the heart is arrested and the patient is maintained under cardioplegic arrest and cardiopulmonary bypass. Cardiopulmonary bypass has been shown to be the cause of many of the complications that have been reported in conventional CABG, such as stroke. The period of cardiopulmonary bypass should be minimized, if not avoided altogether, to reduce patient morbidity.

One approach to coronary artery bypass grafting that avoids cardiopulmonary bypass is performing the suturing procedure on a beating heart in a minimally invasive direct coronary artery bypass graft ("MIDCAB") procedure. At present, however, safe, reproducible, and precise anastomosis between a stenotic coronary artery and a bypass graft vessel presents numerous obstacles including continuous cardiac translational motion which makes meticulous microsurgical placement of graft sutures extremely difficult. The constant translational motion of the heart and bleeding from the opening in the coronary artery hinder precise suture placement in the often tiny coronary vessel.

The above mentioned drawbacks of hand suturing have led to the development of various approaches to stitchless vascular connection or anastomosis which has the advantage of quick and simple execution and undamaged vascular endothelium. Some approaches to stitchless anastomosis used rigid rings prepared from various materials. For example, Geotz et al., INTERNAL MAMMARY-CORONARY ARTERY ANASTOMOSIS—A Nonsuture Method Employing Tantalum Rings, J. Thoracic and Cardiovasc. Surg. Vol. 41 No. 3, 1961, pp. 378–386, discloses a method for joining blood vessels together using polished siliconized tantalum rings which are circumferentially grooved. The free end of the internal thoracic artery is passed through a ring chosen according to the size of the stenotic coronary artery. The free end of the thoracic artery is everted over one end of the ring as a cuff and fixed with a silk ligature which is tied around the most proximal of the circular grooves in the ring. The cuffed internal thoracic artery is inserted into an incision in the target coronary artery. The ring is fixed in place and sealingly joined to the target coronary artery by tying one or more sutures circumferentially around the target vessel and into one or more circular grooves in the ring. An intima-to-intima anastomosis results.

The use of metallic coupling rings is also disclosed in Carter et al., Direct Nonsuture Coronary Artery Anastomosis in the Dog, Annals of Surgery, Volume 148, No. 2, 1958, pp. 212–218 (describing use of rigid polyethylene rings for stitchless vascular connections). Moreover, for example, U.S. Pat. No. 4,624,257 to Berggren et al. describes a device consisting of a pair of rigid rings each having a central opening through which the end of the coronary or graft vessel is drawn and everted over the rings. A set of sharp pins extends outwardly from the face of each ring and pierce through the vessel wall in the everted configuration. The rings are then joined together to align the end of the graft vessel with the opening in the target vessel.

However, no permanently satisfactory results have been reported with the use of rigid rings. A rigid ring presents a foreign body of relatively heavy weight which does not heal well and produces pressure necrosis. Moreover, the use of rigid rings that completely encircle the graft vessel and the arteriotomy creates a severe "compliance mismatch" relative to both the coronary artery and the graft vessel at the anastomosis site which could lead to thrombosis. That is, recent studies suggest that the anastomosis site should not be dramatically different in compliance relative to either the coronary artery or the vascular graft, which is the case when using rigid rings to sealingly join two vessels together.

Another method currently available for stitchless anastomosis involves the use of stapling devices. These instruments are not easily adaptable for use in vascular anastomosis. It is often difficult to manipulate these devices through the vessels without inadvertently piercing a side wall of the vessel. Moreover, as noted above, the scale of the vessels is extremely small, and it is extremely difficult to construct a stapling device that can work reliably on such a small scale to provide a consistent and precise leak-free vascular anastomosis.

In response to the inherent drawbacks of previous devices and methods for performing vascular anastomoses, the applicant has invented a novel device and method for anastomosing vessels using deformable or curable materials, which can be molded in vivo to create a shaped article which is capable of sealingly joining a graft vessel to a target vessel in a patent, compliant anastomosis. The application of deformable materials to body tissues of humans to treat various medical conditions has become increasingly important in medicine. By "deformable," it is meant that the material may be transformed from a solid, non-fluent state to a moldable, fluent state in vivo upon the application of energy, such as light energy or heat, to the material. The deformable material, for example, may become moldable in vivo by a heat-activated process upon the application of radiant energy from an energy source such as a radio frequency energy source, microwave energy source, ultrasonic energy source, or light energy source at a predetermined frequency, wavelength or wavelengths. Alternatively, the deformable material may become moldable by other conventional heat-activated heating means, such as by conductive heating or convective heating. In addition, deformable materials that become moldable by a non-thermal light-activated process without generating heat also are generally known. Such materials can be converted to a moldable, fluent state by any one of a number of light-activated processes, such as a photochemical process or a photophysical process (i.e., photoacoustic or plasma formation).

Alternatively, it is also generally known to use curable materials, such as an acrylate or an acrylated urethane material, to bond two materials together, such as body tissue surfaces. A "curable" material refers to a material that can be transformed from a generally fluent, or liquid state, to a solid, non-fluent, cured state upon the application of energy, such as light energy or heat, to the material. The curable material is preferably applied to an internal tissue surface in fluent form, as a liquid or viscous gel. The coated tissue can then be exposed to light, such as ultraviolet, infrared or visible light, or heat, to cure the material and render it non-fluent, in situ. If light is used as the activating medium, the light is selected to be of an appropriate wavelength and intensity to effectively transform the material from its fluent state into its non-fluent state. Heat curable materials can be used in a similar fashion with the method of heating chosen from the list set forth above for deformable materials.

Among the various uses of deformable and curable materials are the prevention of post-operative adhesions, the protection of internal luminal tissue surfaces, the local application of biologically active species, and the controlled release of biologically active agents to achieve local and systemic effects. They may also be used as temporary or long-term tissue adhesives or as materials for filling voids in biological materials. The materials and conditions of application are selected to enhance desirable properties such as good tissue adherence without adverse tissue reaction, non-toxicity, good biocompatibility, biodegradability, and ease of application. Numerous examples of these materials and their various current uses are fully disclosed in U.S. Pat. No. 5,410,016 to Hubbell et al. and U.S. Pat. No. 5,662,712 to Pathak et al., the entire contents of which are expressly incorporated by reference herein. However, it is believed that these materials have not been applied to the field of coronary artery bypass graft surgery, and more particularly, to performing vascular anastomoses. Accordingly, a need exists for a simple method and device for performing a vascular anastomosis using deformable or curable materials in vivo that avoids the problems associated with the prior art methods and devices for joining two vessels together.

SUMMARY OF THE INVENTION

The present invention involves improvements to methods and devices for performing vascular anastomoses using deformable or curable materials in vivo. The invention facilitates sealingly joining a graft vessel, such as an internal thoracic artery, to a target vessel, such as a left anterior descending artery.

A method of the present invention for sealingly joining a graft vessel to a target vessel at an anastomosis site generally includes positioning a fastener made from a deformable material radially adjacent a free end portion of the graft vessel. The material is transformable between a non-fluent state and a fluent state upon application of energy to the material. At least the free end portion of the graft vessel is inserted in the target vessel through the opening in the target vessel. Energy is supplied to the deformable material at an intensity sufficient to transform the material into the fluent state. The free end portion of the graft vessel is radially expanded to expand the graft vessel into intimate contact with an inner wall of the target vessel. The energy supply is discontinued so that the material returns to its non-fluent state to sealingly secure the graft vessel to the target vessel.

In another aspect of the invention, an anastomosis device generally comprises a tubular member formed of a deformable material and a graft vessel connected to the tubular member. The tubular member is transformable upon application of energy to the tubular member between a non-fluent state and a fluent state in which the tubular member is radially expandable to sealingly engage the graft vessel with the target vessel.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

FIG. 1 is a perspective schematic view of an anastomosis device of the present invention showing the formable, moldable tubular member.

FIG. 1A is a perspective schematic view of an alternative embodiment of the anastomosis device of FIG. 1 showing a thin sheet of formable, moldable material.

FIG. 1B shows a pre-formed tubular member.

FIG. 2 shows the anastomosis device of FIG. 1 after positioning the device about an external surface of a free end of the graft vessel.

FIG. 3 is an elevated view of the anastomosis device of FIG. 2 with the free end of the graft vessel everted over a portion of the tubular member.

DESCRIPTION OF THE INVENTION

Figure 4:
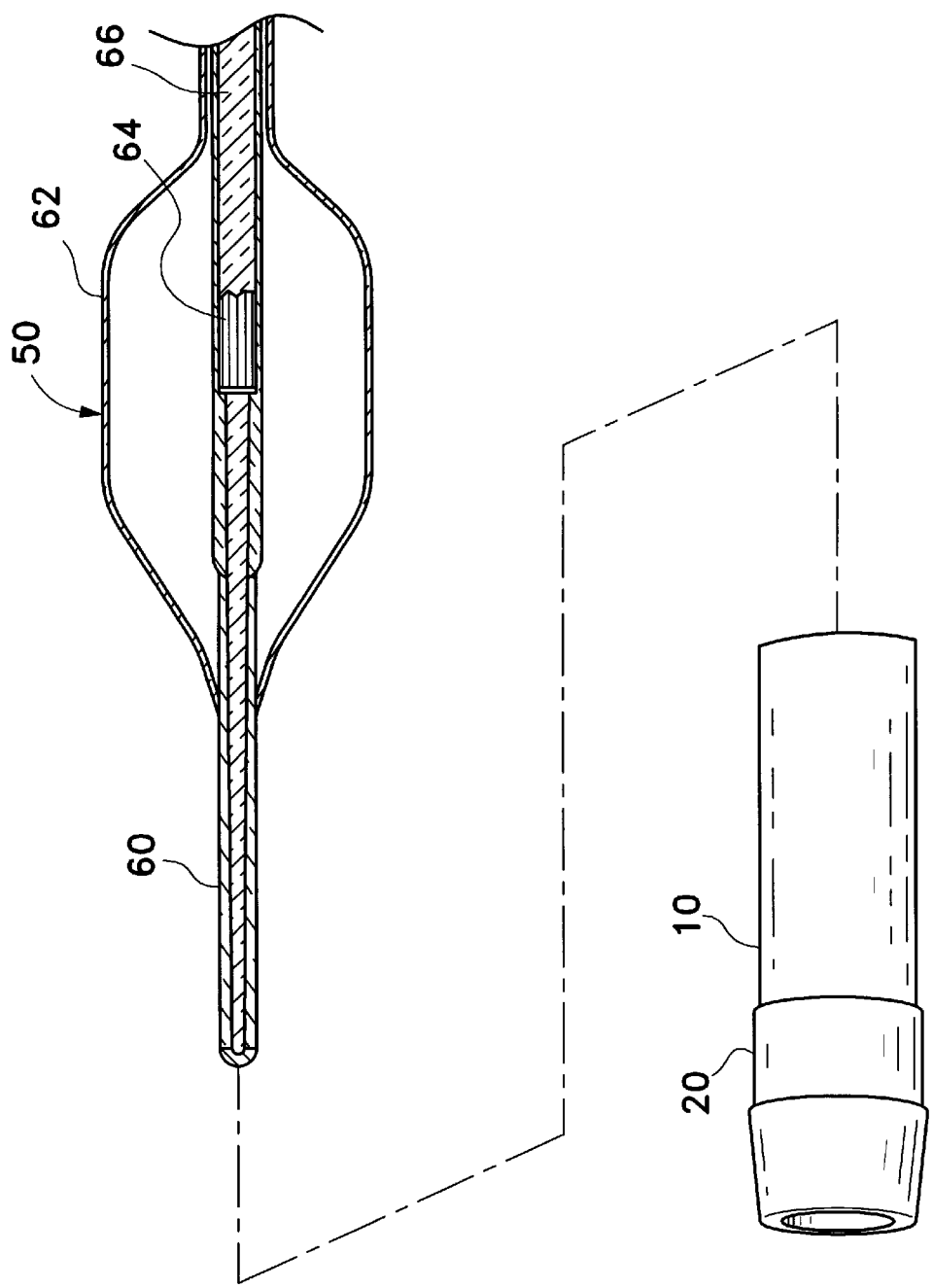
FIG. 4 is an elevated view of the anastomosis device and graft vessel of FIG. 3 and a light-diffusing balloon catheter prior to insertion of the catheter longitudinally into the graft vessel.

Referring now to the drawings, and first to FIG. 1, an anastomosis device constructed according to the principles of the present invention is shown and generally indicated with reference numeral 8. The anastomosis device (or fastener) 8 is used to connect a graft vessel 10, such as a thoracic artery or saphenous vein, to a target coronary vessel 12, such as the left descending artery, in an anastomosis. The anastomosis device 8 of the present invention may also be used in connecting various other vessels or arteries and may be used to connect synthetic vascular grafts to an artery.

The fastener 8 comprises a tubular member 20 as shown in FIG. 1. The tubular member 20 is constructed from a deformable material that must satisfy various criteria such as moldability, strength, biocompatability, and light absorption characteristics. The deformable material may comprise a material that becomes moldable in vivo by a heat-activated process upon the application, for example, of radiant energy from an energy source such as a radio frequency energy source, microwave energy source, ultrasonic energy source, or light energy source at a predetermined frequency, wavelength or wavelengths. Alternatively, the deformable material may become moldable by other conventional heating means, such as by conductive heating or by convective heating. In addition, deformable materials that become moldable by a non-thermal light-activated process without generating heat, such as by a photochemical process or a photophysical process (i.e., photoacoustic or plasma formation), also are contemplated for use in the present invention.

The deformable material should become moldable or fluent at a condition such as temperature that is not significantly injurious to tissue or surrounding fluids if maintained at that condition for the amount of time needed to implant and shape the material. Additionally, if temperature is the germane condition, the material should become moldable at a temperature above about 40 degrees C., since that temperature is greater than a person's body temperature with hyperthermia or fever (approximately 38 to 40 degrees C.). The minimum molding temperature prevents the material from spontaneously softening or melting in response to elevated, physiologically occurring body temperatures.

It is also preferred that the deformable material have a substantially crystalline or semi-crystalline structure so that when irradiated and transformed into its moldable, fluent state, it will undergo a rapid transition to a viscous fluid that will flow readily, yet remain cohesive, when subjected to molding forces. The materials used in this invention are termed "fluent" when in their moldable state. The actual viscosity of the fluent material that allows the material to be molded without significant mechanical disruption of the tissue depends on the particular tissue and the method by which the material is molded. In general, it is preferred that the material be such that once rendered fluent, the material may be shaped or formed using a physiologically acceptable amount of force to reduce damage to surrounding tissue during the molding process. The material must also be structurally sound in its non-fluent, or solid form, to provide mechanical support and strength to withstand forces exerted upon the shaped material during its functional lifetime in vivo at the anastomosis site. This requirement is important if the material is also bioerodable after its functional lifespan. The material can include one or more predefined perforations or apertures (not shown) once transformed from a delivery configuration to its final, shaped support configuration. The perforations may allow increased flexibility to facilitate delivery and reduce tissue erosion during and after implementation, and increase ingrowth of tissue for anchoring and encapsulation of the material.

Where light energy is used as the heat activating medium (i.e., for a photothermal process), the deformable material should preferably absorb light within a wavelength range that is not absorbed significantly (from a clinical perspective) by tissue, blood, physiological fluids, or water. Wavelengths in the ultraviolet, visible, and infrared spectrum may be used, for example, to selectively heat the material to its molding temperature. Ultraviolet light typically has a wavelength of between about 100 and 400 nm, visible light has a wavelength typically in the range of between about 400 and 700 nm, and infrared light typically has a wavelength of between about 700 and 15,000 nm. Additionally, a chromophore such as a dye or pigment may be incorporated into the material to selectively absorb light at a predefined, specific wavelength. As an alternative to compounding the material with a chromophore, polymers or copolymers that naturally absorb the wavelength spectrum of the light may be used and the mechanism of action can be either photothermal or photochemical as explained above. Preferably, one or more of a wide variety of therapeutically useful pharmacological agents may be impregnated into the material, thus providing local drug delivery to prevent thrombus formation, smooth muscle cell proliferation, or inflammatory responses. Examples of such drugs include anti-platelet or anti-thrombus agents (such as Heparin, Hirudin, tPA, Streptokinase, Urokinase, Persantine, Aspirin, etc.), anti-inflammatory agents (such as steroidal and non-steroidal compounds), and anti-proliferative compounds (such as suramin, monoclonal antibodies for growth factors, and equivalents). In addition, other potentially useful drugs can be impregnated into the material to facilitate healing and reduce the incidence of thrombosis at the anastomosis site, such as immunosuppressant agents, glycosaminoglycans, collagen inhibitors, and endothelial cell growth promoters.

The deformable material is also preferably bioerodable. By "bioerodable", it is meant that the material will be broken down in the body and gradually absorbed or eliminated by the body after its functional lifespan, which in the case of the structural support application of the present invention preferably is between 3 to 24 months, although shorter or longer periods may be appropriate depending on the particular application for the fastener 8. Once the material has been absorbed by the body, the graft will exhibit similar compliance to that of the native artery. The new tissue ingrowth forms a natural biological field between the graft vessel and the target vessel. The new tissue growth connects the graft vessel to the target vessel so that the fastener is no longer required.

Examples of deformable materials which may be used in the present invention and which typically satisfy the above criteria include suitable polymers and copolymers, or combinations thereof, such as polyglycotic/polylactic acid (PGLA), polyhydroxybutylate valerate (PHBV), polycaprolactone (PCL), polycaprolactone homopolymers and copolymers, and the like. Many of these materials (and other similar materials) are fully described in U.S. Pat. No. 5,662,712 to Pathak et al., the entire contents of which are incorporated herein by reference.

Polycaprolactone homopolymers and copolymers, for example, possess adequate strength in their solid form to structurally support soft tissue lumens. Additionally, once positioned and molded to a desired shape in a body lumen or about a vessel, the physical structure of such materials is sufficiently nonvariable, in the period prior to their bioerosion, to maintain constant dimensions in their molded state. Polycaprolactones have a crystalline melting point of approximately 60 degrees C., and can be deployed in vivo using the method described in detail below. Additionally, such polymeric materials in their fluent state are well adapted for mechanical deformation to various degrees and into various configurations. Polcaprolactone homopolymers and copolymers can be designed to resorb as soon as three months after implantation, which may be preferable for the application of the fastener 8. For example, polycaprolactone copolymerized with lactic or glycolic acids may resorb over a 3 to 9 month period. Additionally, other bioabsorbable, deformable materials which have higher melting temperatures, such as polyglycolides and polylactides, may be used since these materials have glass transition temperatures on the order of about 45 degrees C. which makes them moldable at physiologically acceptable temperatures. These examples are in no way meant to be limiting, however, and any deformable, moldable material that satisfies the criteria described above may be used in the present invention without departing from the scope of the invention. Any of the methods known in the art of polymer processing may be used to form the polymeric material into the tubular shape of FIG. 1 and, if necessary, to compound chromophores into the material.

The diameter of the tubular member 20 will vary depending on the size of the graft vessel about which it is positioned. Preferably, the inner diameter of the tubular member 20 will generally be between about 0.5 to 6.0 mm for a coronary anastomosis. The length of the tubular member 20 can also vary, and is preferably between 4 and 20 mm in length, for example. Alternatively, as shown in FIG. 1A, the fastener 8 may comprise a relatively thin sheet of material 30 that can be conformed about an external surface of the graft vessel 10 prior to the anastomosis procedure described below. The sheet 30 may be rolled about the graft vessel 10. The adhesiveness of the material allows the edges of the sheet 30 to adhere to one another. If required additional adhesive may be applied to one or both of the edges of the sheet. Upon irradiation and subsequent expansion of the material, the sheet 30 will be caused to unroll to press the graft vessel 10 into conforming contact with the target vessel 12. Further alternatively, as shown in FIG. 1B, the fastener 8 may comprise a pre-shaped tubular member 32 which will at least have a first bend along its length such that a portion of the tubular member extends at an angle "R" of between about 30° and 40° from a longitudinal centerline, the pre-shaped tubular member 32 provides support for the graft vessel through the anastomosis site after employment of the device to prevent kinking of the graft vessel.

FIGS. 2–7 show an exemplary use of the anastomosis device 8 of the present invention in an open surgical coronary artery bypass graft procedure via a median or partial sternotomy. The anastomosis device 8 of this example is preferably formed from a heat-activated deformable material, although a non-thermal light-activated deformable material can be used as well without departing from the scope of the invention. This example is meant to be by illustration only, and in no way is meant to be limiting. The present invention can be used in other cardiac surgery procedures such as minimally invasive direct coronary artery bypass grafting (MIDCAB) on a beating heart though a small incision (thoracotomy) (about 6–8 cm) in the left side of the chest wall, in endoscopic minimally invasive cardiac surgery bypass graft procedures, and in other vascular procedures to join two vessels together. By way of example, the left internal thoracic artery is used as the graft vessel 10. In this example, the left anterior descending artery is used as the target vessel 12 and contains a build-up of plaque or narrowing 13. If left untreated, this diseased artery may lead to insufficient blood flow and eventual angina, ischemia, and possibly myocardial infarction.

Conventional coronary bypass graft procedures require that a source of arterial blood be prepared for subsequent bypass connection to the diseased artery. An arterial graft can be used to provide a source of blood flow, or a free vessel graft may be used and connected at the proximal end to a source of blood flow. Preferably, the source of blood flow is any one of a number of existing arteries that are dissected in preparation for the bypass graft procedure. In many instances, it is preferred to use either the left or right internal thoracic artery. In multiple bypass procedures, it may be necessary to use free graft vessels such as the saphenous vein, gastroepiploic artery in the abdomen, and other arteries harvested from the patient's body as well as synthetic graft materials, such as Dacron or Gortex grafts. If a free graft vessel is used, the upstream end (proximal) of the dissected vessel, which is the arterial blood source, will be secured to the aorta to provide the desired bypass blood flow, and the downstream end (distal) of the dissected vessel will be connected to the target vessel in a distal anastomosis.

In order to perform an anastomosis with the fastener 8 of the present invention, the graft vessel 10 preferably is first coupled to the fastener 8. Preferably, the graft vessel 10 is coupled to the fastener 8 by first inserting a free end of the graft vessel 10 through an opening in the tubular member 20 and moving the graft vessel 10 longitudinally within the tubular member 20 until the free end of the graft vessel extends a short distance beyond an end of the tubular member as shown in FIG. 2. Preferably, the free end of the graft vessel 10 is then everted over an end of the tubular member 20 as shown in FIG. 3. The natural adhesiveness of graft vessel 10 or tubular member 20 may be sufficient to secure the graft vessel 10 to the tubular member 20. If necessary, one or more sutures can be applied between the graft vessel 10 and the tubular member 20 to secure the graft vessel 10 to the fastener 8 in an everted configuration. Alternatively, the graft vessel 10 can be secured to the tubular member 20 with glue, other adhesive means, by tying one or more sutures circumferentially around the graft vessel 10, or by any other suitable means.

Where light energy is used as the heat activating medium, a suitable light-diffusing balloon catheter device 50 which has the ability to deliver light energy to luminal surfaces such as blood vessels is inserted through the lumen of the graft vessel 10 and fastener 8. An example of a suitable light-diffusing balloon catheter device 50 is shown in U.S. Pat. No. 5,441,497 to Narciso et al., the entire contents of which are incorporated by reference herein, although other suitable light-diffusing balloon catheter devices may also be used, such as that disclosed in Spears U.S. Pat. No. 4,773,899, for example. Additionally, a separate light diffusing catheter (or guidewire) and balloon catheter (not shown) may be used in conjunction with one another, as disclosed, for example, in Spears U.S. Pat. No. 5,199,951, the entire contents of which are incorporated by reference herein. Generally, the light-diffusing balloon catheter 50 includes a light diffusing guidewire 60 which is used in conjunction with an inflated balloon 62. The balloon 62 is affixed to the guidewire 60 so that the balloon 62 overlies the light diffusing member 64 of the guidewire 60. The wall of the balloon 62 is transparent at the wavelength of light being delivered to (or received from) the surrounding tissue. At least one optical fiber 66 delivers light from an external light source (not shown) to the light diffusing member 64. The light diffusing member 64 within balloon 62 is selected for optimum transmission of light with maximum light scattering.

Figure 5:
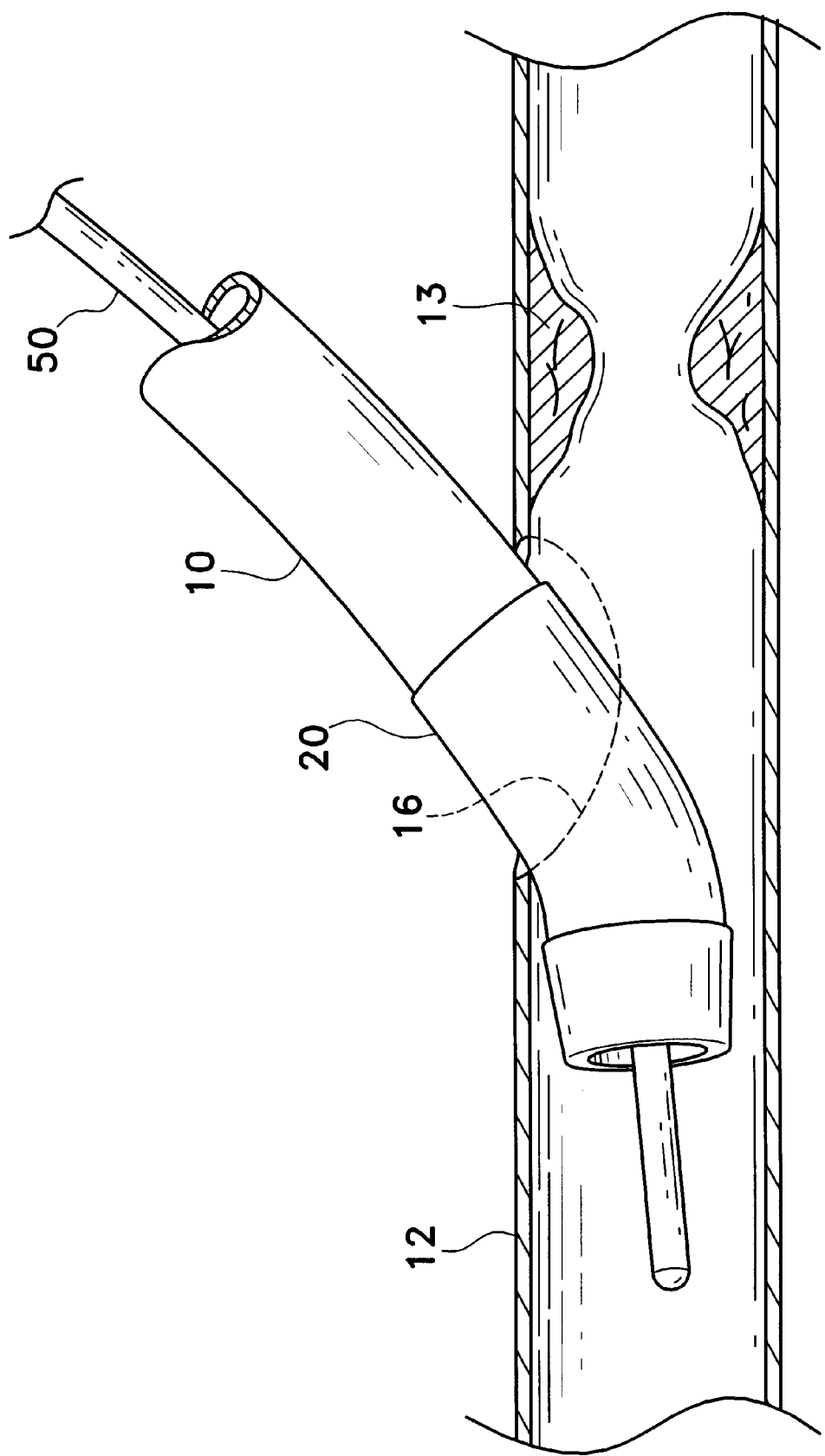
FIG. 5 is an elevated view of the anastomosis device of FIG. 4 and balloon catheter inserted into the target vessel through an incision in the target vessel.
Figure 6:
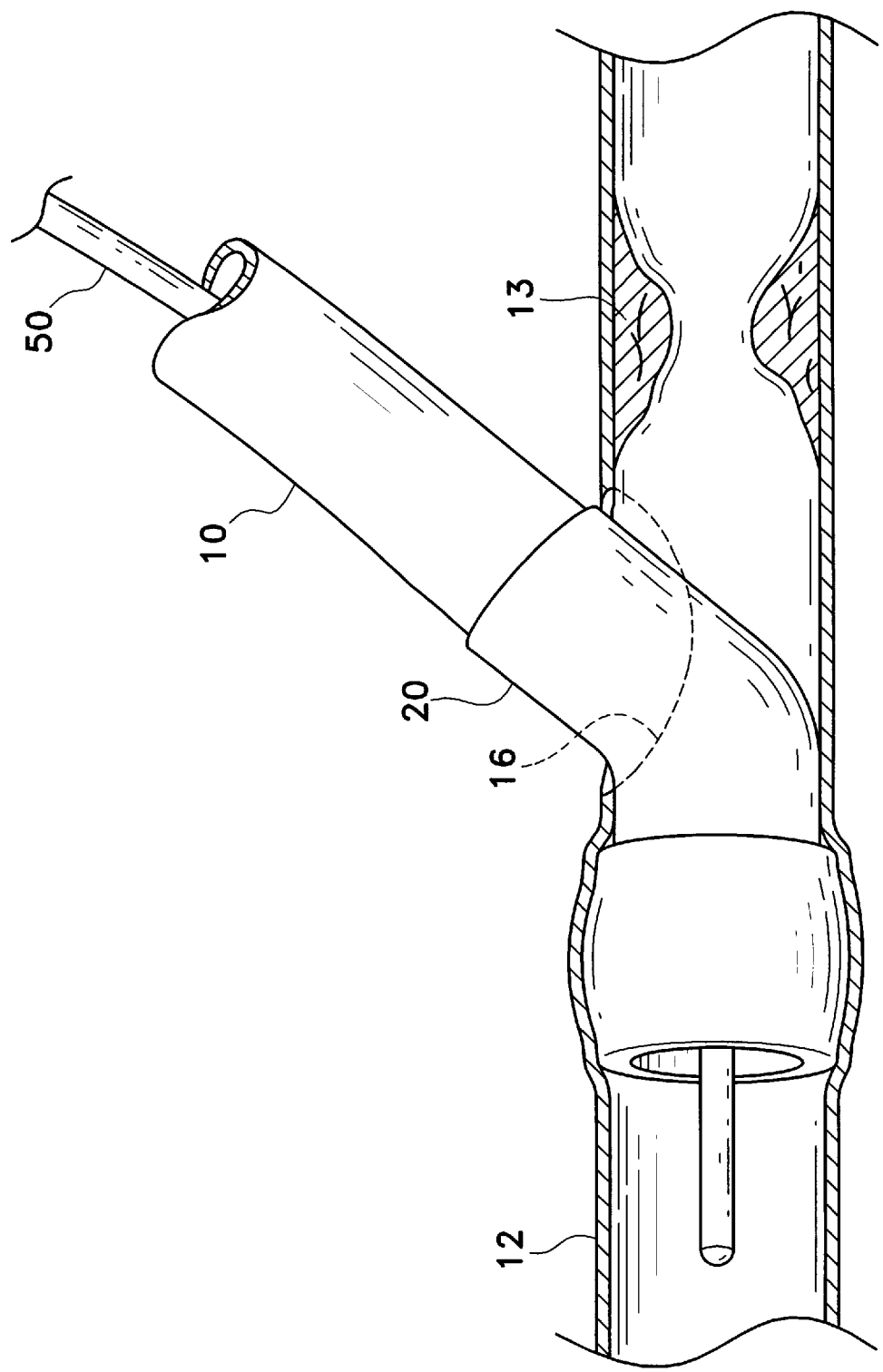
FIG. 6 is an elevated view of the anastomosis device of FIG. 5 following light irradiation and radial expansion of the balloon.
Figure 7:
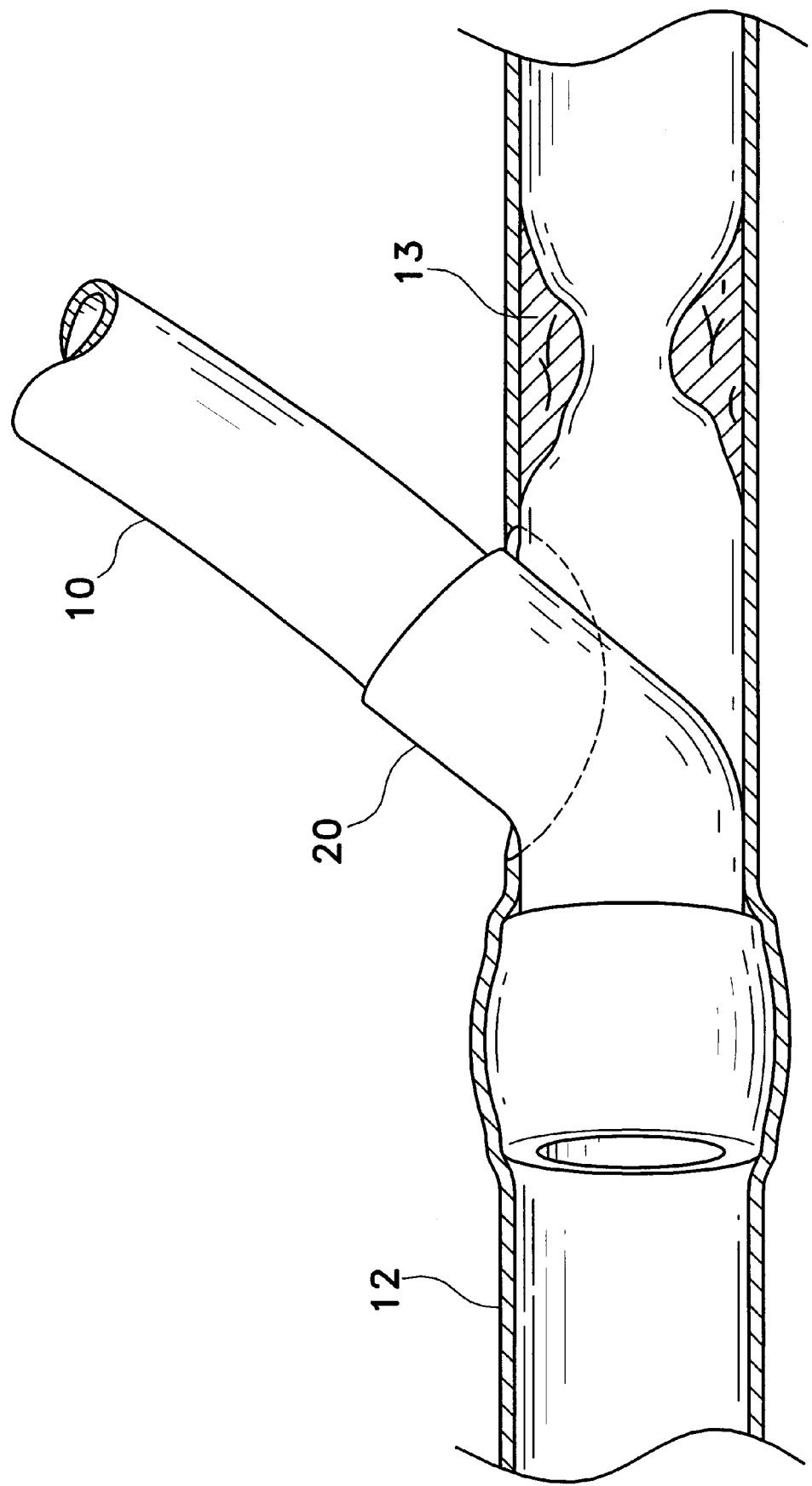
FIG. 7 is an elevated view of the anastomosis device of FIG. 6 after the light-diffusing balloon catheter has been removed from the graft vessel showing the completed anastomosis.

The graft vessel 10 is inserted into the target vessel 12 through an incision (opening) 16 in a wall of the target vessel 12. The fastener 8 is preferably positioned in the target vessel 12 such that at least an end portion of the tubular member 20 extends generally coaxial with the target vessel 12 (FIG. 5). With the fastener 8 securely positioned in the target vessel 12, light energy at a given wavelength or wavelengths is supplied to the light diffusing member 64 from the energy source via optical fiber 66 to irradiate, or illuminate, the tubular member 20 with light at a wavelength or wavelengths at which the deformable material readily absorbs. Upon absorption of the light energy, the deformable material forming tubular member 20 is transformed into its moldable state. Alternatively, where heat energy is used as the heat activating medium, the deformable material can be made fluent by use of a suitable thermal balloon catheter (not shown) in lieu of the light-diffusing balloon catheter 50, or by any other conductive or convective heating means as would be obvious to one of ordinary skill in the art, such as by providing a heated saline irrigation flush. Inflation of the balloon 62 causes the tubular member 20 to radially expand outwardly, thereby pressing the graft vessel 10 into conforming engagement with an inner wall of target vessel 12 (FIG. 6). Alternatively, where the deformable material comprises a rolled sheet 30 such as in FIG. 1A which can be reconfigured prior to molding, the material is reconfigured using the balloon and then irradiated to transform it into its moldable state to mold it into conformance with the everted graft vessel 10 and target vessel 12. By discontinuing the supply of light energy from the energy source, the deformable material will become non-fluent and remain in its molded configuration. The balloon 62 is then deflated and the catheter device 50 withdrawn from the graft vessel 10 (FIG. 7).

The engagement of the graft vessel 10 via tubular member 20 with the inner wall of the target vessel 12 prevents substantial longitudinal movement of the tubular member 20 within the target vessel. The tubular member 20 in its molded configuration will apply a gentle uniform, circumferential pressure against the everted graft vessel 10 and the inner wall of the target vessel 12. An intima-to-intima anastomosis results. The flexibility of the tubular member 20 permits the fastener device 8 to be substantially compliant with the target vessel 12 and the graft vessel 10 to reduce thrombosis formation. Additionally, the tubular member 20 is preferably bioerodable, so that after its functional lifespan (i.e., 3 to 24 months), it will degrade and leave remaining a natural patent, sealed, compliant anastomosis.

If required, cardiac stabilization such as described in co-pending provisional patent application for Compositions, Apparatus and Methods For Facilitating Surgical Procedures, filed Aug. 8, 1997 and invented by Francis G. Duhaylongsod, M.D, may be used during the procedure. Other pharmacological or mechanical methods may also be used.

In an alternative embodiment of the present invention, a different fastener device is disclosed for sealingly joining a graft vessel to a target vessel at an anastomosis site. The fastener (not shown) of this embodiment comprises a coating of a fluent, curable material, such as a liquid or viscous gel, which is applied to an external surface of a free end portion of the graft vessel 10. Examples of suitable curable materials include, but are not limited to, light-curable materials such as the chemical class of biocompatible compounds including acrylate polymers which can be cured when exposed to ultraviolet light, and acrylate urethane polymers which can be cured when exposed to ultraviolet light and/or visible light of sufficient intensity. These materials also can be combined with a dye that absorbs light at a very specific wavelength so that light energy can be used to selectively and rapidly cure the material and not heat the surrounding tissue.

Other suitable light-curable materials may include bioerodable hydrogels which can be photopolymerized (or gelled) in vivo by a brief exposure to long wavelength ultraviolet light, such as polyethylene-glycol (PEG) based hydrogels as fully disclosed in U.S. Pat. No. 5,410,016 to Hubbell et al. Several biocompatible, photopolymerizable macromer hydrogels are disclosed in U.S. Pat. No. 5,410,016 (see, for example, Table I therein) which are suitable as tissue supports by forming shaped articles within the body upon the application of light energy at a specific wavelength. These macromers, for example, can be composed of degradable co-monomers such as glycolides, lactides, and caprolactones of various molecular weights and compositions. These materials are given by way of example only, and in no way are meant to limit the invention to the specific materials disclosed. Any suitable light-curable material having the requisite strength, biocompatability and moldability criteria may be used without departing from the scope of the present invention. In addition, heat-curable materials can be used in a similar fashion with the method of heating chosen from the list set forth above for deformable materials, such as convective or conductive heating.

As in the previous example, the curable material can be impregnated with one or more anti-platelet or anti-thrombus agents, anti-inflammatory agents, and anti-proliferative compounds. In addition, other potentially useful drugs can be impregnated into the material to facilitate healing and reduce the incidence of thrombosis at the anastomosis site, such as immunosuppressant agents, glycosaminoglycans, collagen inhibitors, and endothelial cell growth promoters. Preferably, where light-curable materials are used, wavelengths in the ultraviolet, visible, and infrared light spectrum may be used, for example, to transform the curable material into its cured state, since light energy within these wavelengths is not significantly injurious to surrounding tissues. Additionally, a chromophore such as a dye or pigment may be incorporated into the material to selectively absorb light at a predefined, specific wavelength or wavelengths.

The method of using the fastener of this embodiment is similar in many respects to that shown for use of the tubular member 20 of FIGS. 1–7, with the principal difference being that the energy supply and balloon expanding steps are typically reversed. In this alternative embodiment, after the coating of curable material is applied to an external surface of the free end portion of the graft vessel 10, the free end portion of the graft vessel 10 is everted. The curable material typically has a natural adherent property in which case the free end portion of the graft vessel 10 in its everted configuration will be adhered and secured to the coating material. If necessary, one or more sutures may be required to retain the free end of the graft vessel 10 in an everted configuration. Subsequently, where a light-curable coating material is used, a light-diffusing balloon catheter 50 such as shown in FIG. 4 preferably is inserted into the graft vessel 10. Alternatively, as above, a separate light diffusing catheter (or guidewire) and balloon catheter (not shown) may be used in conjunction with one another.

At least a portion of the everted free end portion of the graft vessel 10 is then positioned in the target vessel 12 through an incision 16 in the target vessel 12. The balloon 62 of light-diffusing balloon catheter 50 is then inflated to radially expand at least the free end portion of the graft vessel 10 into conforming engagement with an inner wall of the target vessel 12. Once expanded, curing is achieved by irradiating, or illuminating, the free end portion of the graft vessel 10 with light energy at a predetermined wavelength or wavelengths supplied by an energy source coupled to the light diffusing member 64 of light-diffusing balloon catheter 50. The light energy preferably has a wavelength and intensity which does not have a significant adverse effect on the surrounding tissue, such as light within the ultraviolet, infrared, or visible light spectrum. The intensity of the light energy is sufficient to transform the curable material into its cured, non-fluent state to complete the anastomosis. The balloon 62 can then be deflated and the light-diffusing balloon catheter 50 removed from the graft vessel 10. Again, an intima-to-intima anastomosis results which reduces the possibility of thrombosis formation at the anastomosis site. Alternatively, where a heat-curable coating material is used, the curable material can be cured by use of a suitable thermal balloon catheter (not shown) in lieu of the light-diffusing balloon catheter 50, or by any other conductive or convective heating means as would be obvious to one of ordinary skill in the art, such as by providing a heated saline irrigation flush.

Figure 8:
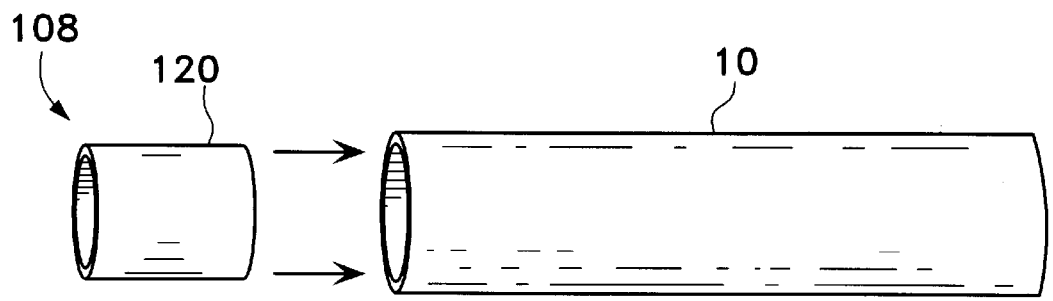
FIG. 8 is an elevated view of an alternative embodiment of an anastomosis device prior to insertion into a graft vessel.
Figure 9:
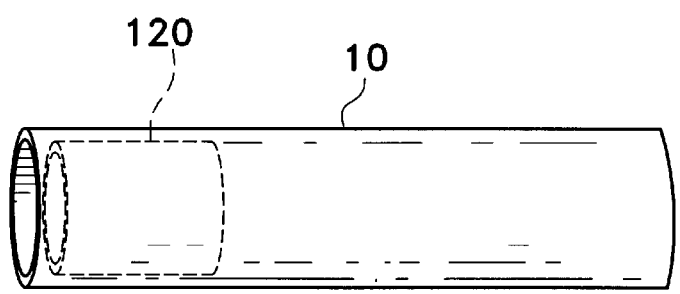
FIG. 9 shows the anastomosis device of FIG. 8 after insertion of the device into the graft vessel.
Figure 10:
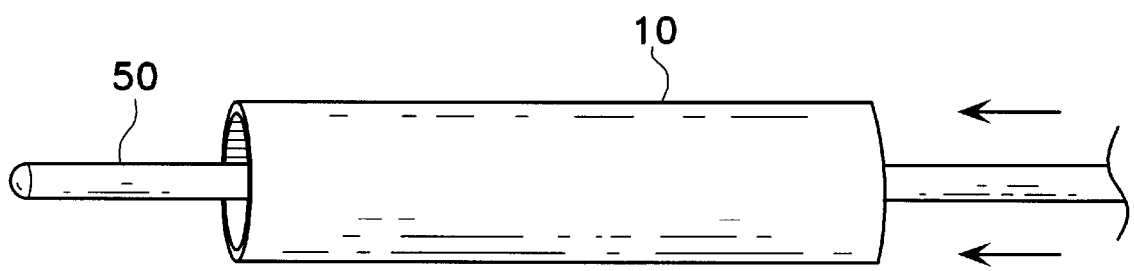
FIG. 10 is an elevated view of the anastomosis device of FIG. 8 with a light-diffusing balloon catheter inserted into the graft vessel and the device.
Figure 11:
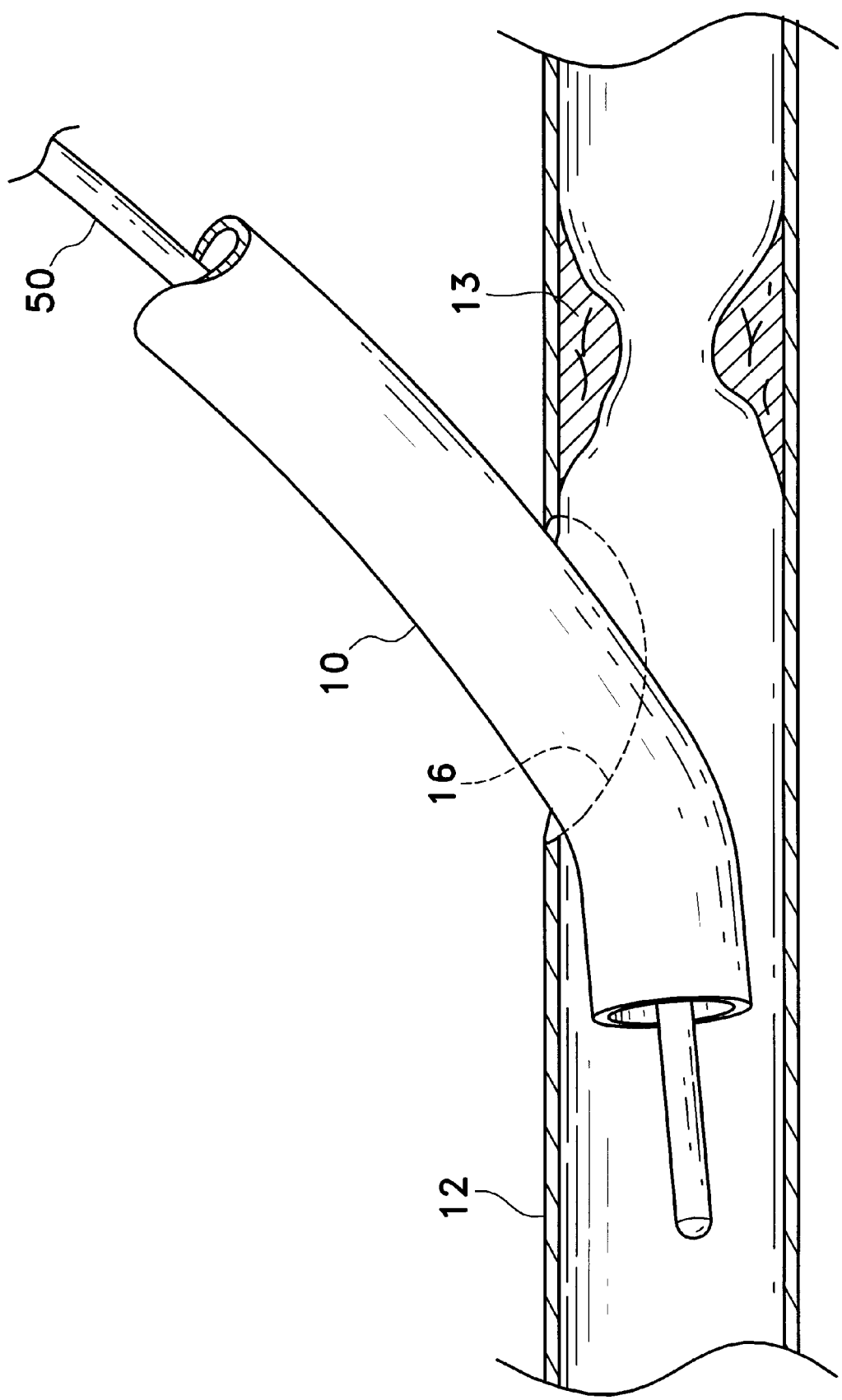
FIG. 11 is an elevated view of the anastomosis device, graft vessel and catheter of FIG. 10 inserted into the target vessel through an incision in the target vessel.
Figure 12:
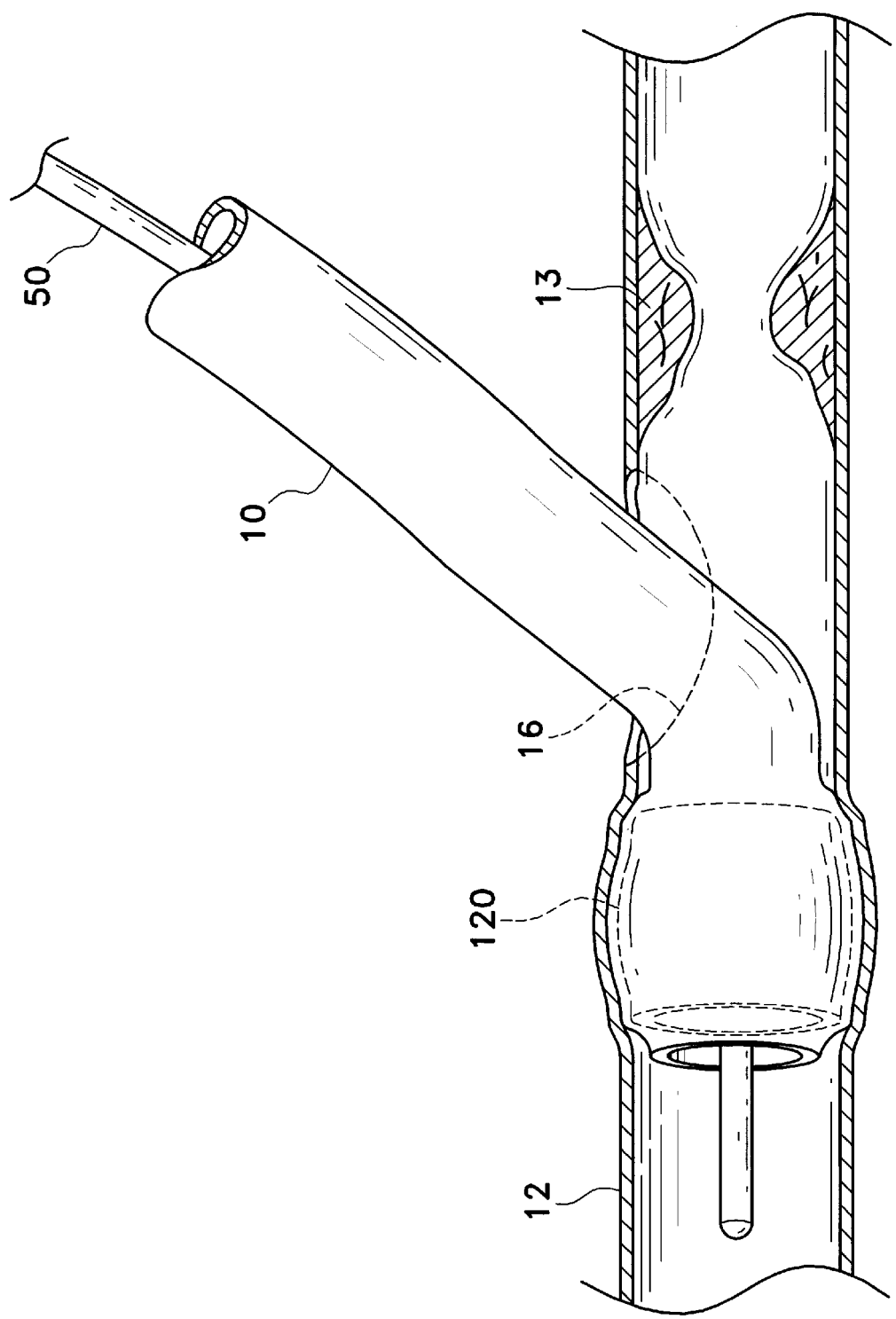
FIG. 12 is an elevated view of the anastomosis device of FIG. 11 following light irradiation and expansion of the balloon.

In alternative embodiments of the invention, the anastomosis fastener can comprise either a tubular member formed of a deformable material or a coating of a curable material that is applied to the internal wall of a free end portion of graft vessel 10. In the case of the embodiment shown in FIGS. 8–13, the fastener 108 comprises a tubular member 120 having a diameter sized to permit the tubular member 120 to be inserted longitudinally into the graft vessel 10, as shown in FIGS. 8–9. As shown in FIG. 10, where a light-activated deformable material is used, a light-diffusing balloon catheter 50 can then be inserted into the graft vessel 10 and the tubular member 120 and positioned such that the balloon (not shown) of the light-diffusing balloon catheter 50 is adjacent an internal surface of tubular member 120. If necessary, the balloon can be partially inflated to secure the tubular member 120 in place prior to inserting the graft vessel 10 into the target vessel 12. With the tubular member 120 securely in place within the free end portion of the graft vessel 10, the graft vessel 10 is then inserted into the target vessel 12 such that at least the free end portion of the graft vessel 10 extends generally coaxial with the target vessel 12, as shown in FIGS. 11–12.

Figure 13:
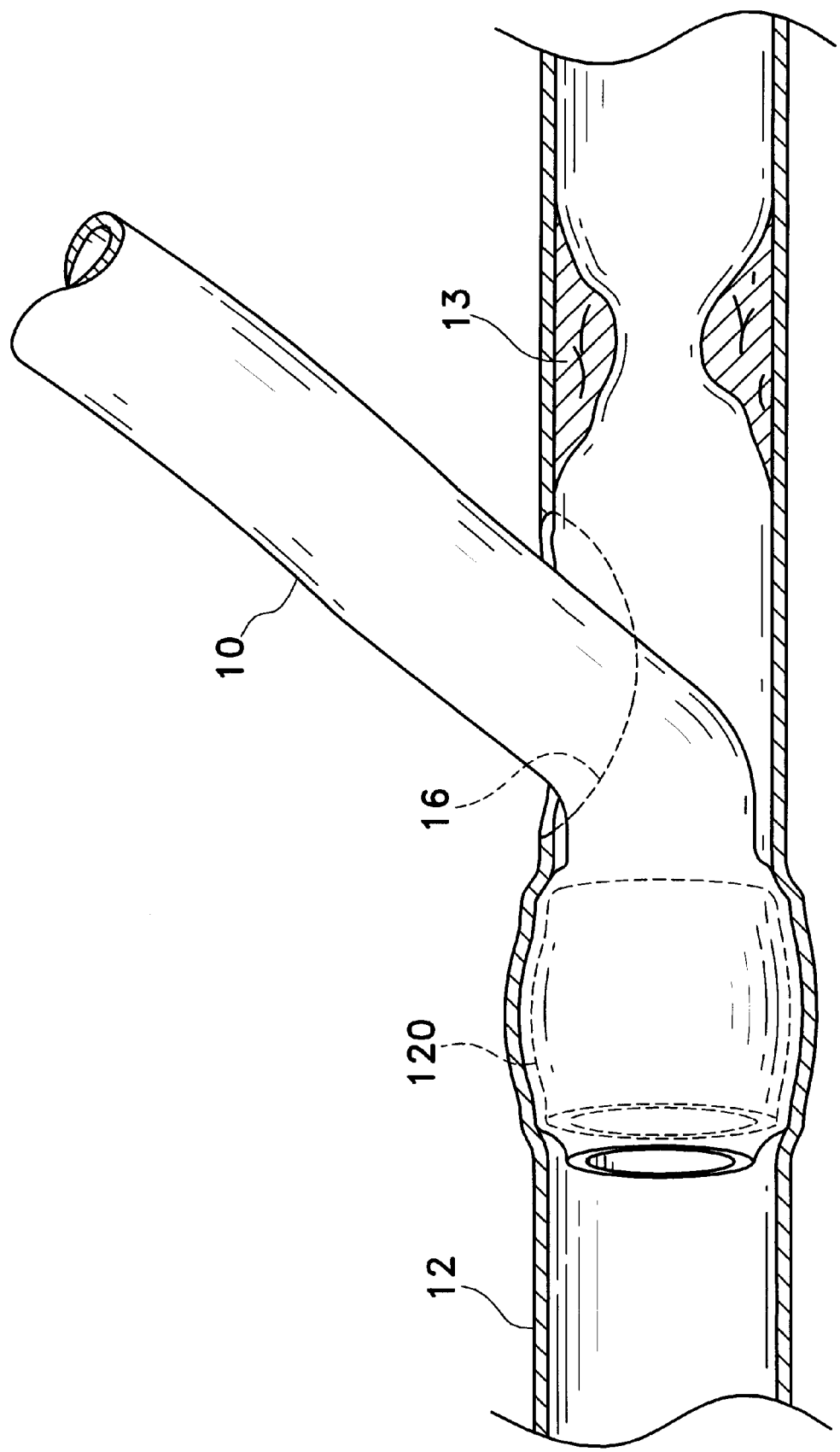
FIG. 13 is an elevated view of the anastomosis device of FIG. 12 after the light-diffusing balloon catheter has been removed from the graft vessel showing the completed anastomosis.

With the graft vessel 10 securely positioned in the target vessel 12, light at a given wavelength or wavelengths is supplied by the light-diffusing balloon catheter 50 to irradiate, or illuminate, the tubular member 120 with light at a wavelength or wavelengths at which the material readily absorbs. Upon absorption of the light, the material forming tubular member 120 is irradiated to transform it into its fluent, moldable state. Further inflation of the balloon causes the moldable tubular member 120 to radially expand outwardly, thereby pressing the graft vessel 10 into conforming engagement with an inner wall of target vessel 12. By discontinuing the supply of light energy from the light source, the formable material will become non-fluent and remain in its molded configuration. The balloon is then deflated and the catheter device 50 withdrawn from the graft vessel 10, as shown in FIG. 13. An intima-to-adventitia anastomosis results.

Alternatively, a coating of a curable material can be applied to an internal wall of the free end portion of the graft vessel 10. In this particular embodiment, the balloon 62 will be expanded fully prior to applying light energy, or heat, to the coating material. Where a light-curable coating material is used, with the graft vessel in conforming engagement with the target vessel 12, curing is achieved by irradiating, or illuminating, the free end portion of the graft vessel 10 with light energy at a predetermined wavelength or wavelengths supplied by an energy source coupled to the light diffusing member of the light-diffusing balloon catheter 50. The intensity of the light energy is sufficient to transform the curable material into its cured, non-fluent state to complete the anastomosis. The balloon can then be deflated and the light-diffusing balloon catheter 50 removed from the graft vessel 10.

The engagement of the graft vessel 10 via tubular member 120 (or the cured, non-fluent coating of curable material) with the inner wall of the target vessel 12 prevents substantial longitudinal movement of the graft vessel 10 within the target vessel 12. The tubular member 120 (or the cured, non-fluent coating) in its molded configuration will apply a gentle uniform, circumferential pressure against the graft vessel 10 and the inner wall of the target vessel 12. The flexibility of the tubular member 120 (or the cured, non-fluent coating) permits the fastener device 108 to be substantially compliant with the target vessel 12 and the graft vessel 10 to reduce thrombosis formation. Additionally, the tubular member 120 (or the cured, non-fluent coating) is preferably bioerodable, so that after its functional lifespan (i.e., 3 to 24 months), it will degrade and leave remaining a natural patent, sealed anastomosis. Although the embodiments of FIGS. 8–13 result in an intima-to-adventitia anastomosis as opposed to an intima-to-intima anastomosis as in the above embodiment of FIGS. 1–7, the anastomosis of these embodiments results in a larger target vessel inner diameter over the previous embodiments, thus increasing the blood flow area, rather than reducing the diameter of the blood flow passage.

It should be understood that while the above is a complete description of the preferred embodiments of the invention, various alternatives, modifications and equivalents may be used. Therefore, the above description should not be taken as limiting the scope of the invention which is defined by the following claims.

All references cited herein are incorporated by reference.

What is claimed is:

1. A method for sealingly joining a graft vessel to a target vessel at an anastomosis site, the target vessel having an opening formed therein, comprising the steps of:

positioning a fastener comprising a deformable material radially adjacent a free end portion of said graft vessel, said material being transformable between a non-fluent state and a fluent state, upon application of energy to the material;

inserting at least said free end portion of said graft vessel in said target vessel through the opening in the target vessel;

supplying energy to the deformable material at an intensity sufficient to transform the material into said fluent state;

radially expanding at least said free end portion of said graft vessel and said fastener to expand the graft vessel into intimate contact with an inner wall of said target vessel; and discontinuing the energy supply so that the material returns to its non-fluent state to sealingly secure the graft vessel to the target vessel.

2. The method of claim 1 wherein said energy is selected from a group consisting of radiant energy, convection heating, conduction heating, light energy, radiofrequency energy, microwave energy, and ultrasonic energy.

3. The method of claim 1 wherein said deformable material is selected from a group consisting of polymerics, polymers, and copolymers.

4. The method of claim 3 wherein said deformable material is selected from a group consisting of polyglycotic/polylactic acid (PGLA) polymer, polyhydroxybutylate valerate (PHBV) polymer, polycaprolactone (PCL) polymer, polycaprolactone homopolymer, and polycaprolactone copolymers.

5. The method of claim 1 wherein said material is bioerodable.

6. The method of claim 1 further comprising the step of everting at least a first portion of said free end portion of the graft vessel over a portion of said fastener prior to said step of inserting the graft vessel in the target vessel.

7. The method of claim 6 wherein the step of everting comprises attaching the first portion of said free end portion of the graft vessel to the fastener.

8. The method of claim 7 wherein the step of attaching the graft vessel to the fastener comprises suturing the graft vessel to the fastener.

9. The method of claim 7 wherein the step of attaching the graft vessel to the fastener comprises applying an adhesive material to an external surface of said first portion of said free end portion of the graft vessel.

10. The method of claim 7 wherein said deformable material has an adhesive surface and the step of attaching the graft vessel to the fastener comprises adhering the first portion of the free end portion of the graft vessel to the fastener.

11. The method of claim 1 wherein said supplying energy step comprises positioning a distal end portion of a light-diffusing balloon catheter in said graft vessel.

12. The method of claim 1 wherein said supplying energy step comprises positioning a distal end portion of a thermal balloon catheter in said graft vessel.

13. The method of claim 11 wherein said supplying energy step further comprises irradiating said deformable material with light energy from an energy source which is coupled to a light-diffusing end member of said catheter via at least one optical fiber.

14. The method of claim 13 wherein said radially expanding step comprises inflating a balloon of said balloon catheter.

15. The method of claim 1 wherein said supplying energy step comprises positioning a distal end portion of a light-diffusing catheter in said graft vessel.

16. The method of claim 15 wherein said supplying energy step further comprises irradiating said deformable material with light energy from an energy source which is coupled to a light-diffusing end member of said catheter via at least one optical fiber.

17. The method of claim 1 wherein said radially expanding step comprises inflating a balloon of a balloon catheter.

18. The method of claim 1 wherein said supplying energy step comprises exposing said material to energy having a wavelength of between 100 nm and 15,000 nm.

19. The method of claim 1 wherein said supplying energy step comprises exposing said material to energy having a wavelength of between 300 nm and 1100 nm.

20. The method of claim 1 wherein said fastener positioning step comprises positioning a tubular sleeve of said deformable material over an external surface of said free end portion of said graft vessel.

21. The method of claim 1 wherein said fastener positioning step comprises rolling a thin sheet of said deformable material over an external surface of said free end portion of said graft vessel.

22. The method of claim 1 wherein said fastener positioning step comprises longitudinally inserting a tubular sleeve of said deformable material within an opening in said free end portion of said graft vessel.

23. The method of claim 1 wherein said radially expanding step is performed prior to said energy supplying step.

24. The method of claim 1 wherein the material is impregnated with one or more agents selected from the group consisting of anti-platelet, anti-thrombus, and antiinflammatory compound.

25. The method of claim 1 wherein the material utilized is impregnated with one or more anti-proliferative compounds.

26. A method for sealingly joining a graft vessel to a target vessel at an anastomosis site, the target vessel having an opening formed therein, comprising the steps of:
   applying a coating comprising a curable material to a free end portion of said graft vessel, said material being transformable between a fluent state and a non-fluent state upon application of energy to the material;
   inserting at least said free end portion of said graft vessel in said target vessel through the opening in the target vessel;
   radially expanding at least said free end portion of said graft vessel to expand the graft vessel into intimate contact with an inner wall of said target vessel; and
   supplying energy to the material at an intensity sufficient to transform the material into its non-fluent state to sealingly secure the graft vessel to the target vessel.

27. The method of claim 26 wherein said material is bioerodable.

28. The method of claim 26 wherein said material is selected from a group consisting of polyethylene-glycol (PEG) based hydrogel, acrylate, and acrylated urethane.

29. The method of claim 26 wherein said coating comprises a liquid.

30. The method of claim 26 wherein said coating comprises a viscous gel.

31. The method of claim 26 wherein the material is impregnated with one or more agents selected from a group consisting of anti-platelet, anti-thrombus, and anti-inflammatory compounds.

32. The method of claim 26 wherein the material utilized is impregnated with one or more anti-proliferative compounds.

33. The method of claim 26 further comprising the step of everting at least a first portion of said free end portion of the graft vessel over a portion of said coating.

34. The method of claim 33 further comprising the step of coupling said first portion of said free end portion to said coating.

35. The method of claim 34 wherein said coupling step includes suturing said first portion to said graft vessel.

36. The method of claim 34 wherein said curable material has an adhesive surface and wherein said coupling step comprises adhering said first portion to said coating.

37. The method of claim 26 wherein said supplying energy step comprises positioning a distal end portion of a light-diffusing balloon catheter in said graft vessel.

38. The method of claim 37 wherein said supplying energy step further comprises irradiating said material with light energy from an energy source which is coupled to a light-diffusing end member of said catheter via at least one optical fiber.

39. The method of claim 37 wherein said radially expanding step comprises inflating a balloon of said balloon catheter.

40. The method of claim 26 wherein said supplying energy step includes the step of positioning a distal end portion of a light-diffusing catheter in said graft vessel.

41. The method of claim 40 wherein said supplying energy step further comprises irradiating said material with light energy from an energy source which is coupled to a light-diffusing end member of said catheter via at least one optical fiber.

42. The method of claim 26 wherein said radially expanding step comprises inflating a balloon of a balloon catheter.

43. The method of claim 26 wherein said supplying energy step comprises exposing said curable material to ultraviolet radiation from an ultraviolet radiation energy source.

44. The method of claim 26 wherein said supplying energy step comprises exposing said curable material to visible light from a visible light energy source.

45. The method of claim 26 wherein said supplying energy step comprises exposing said curable material to infrared radiation from an infrared radiation energy source.

46. An anastomosis device for use in coupling an end of a first vessel to a side of a second vessel in an anastomosis, the device comprising a tubular member formed of a deformable material, and a graft vessel connected to the tubular member, the tubular member being transformable upon application of energy to the tubular member between a non-fluent state and a fluent state in which the tubular member is radially expandable to sealingly engage the graft vessel with the target vessel.

* * * * *